United States Patent [19]

Wilson

[11] Patent Number: 4,854,157
[45] Date of Patent: Aug. 8, 1989

[54] DEVICE FOR MEASURING EFFECTIVE POROSITY

[75] Inventor: Earl Wilson, Ingleside, Ill.

[73] Assignee: The Kendall Company, Boston, Mass.

[21] Appl. No.: 164,679

[22] Filed: Mar. 7, 1988

[51] Int. Cl.⁴ ............................................ G01N 15/08
[52] U.S. Cl. ........................................................ 73/38
[58] Field of Search ...................................... 73/38, 19

[56] References Cited

U.S. PATENT DOCUMENTS

| | | | |
|---|---|---|---|
| 2,861,451 | 11/1958 | Emmons, III | 73/38 |
| 3,251,218 | 5/1966 | Russell | 73/38 |
| 4,191,046 | 3/1980 | Baker et al. | 73/38 |
| 4,213,327 | 7/1980 | Prescott et al. | 73/38 |
| 4,385,517 | 5/1983 | Sorce et al. | 73/38 |

FOREIGN PATENT DOCUMENTS 190640 10/1984 Japan ........................................ 73/38

OTHER PUBLICATIONS

Carr et al; Gas Permeation Analysis Assembly; Technical Disclosure Bulletin, vol. 21, No. 5 (10-1978).

Primary Examiner—Hezron E. Williams
Attorney, Agent, or Firm—Emrich and Dithmar

[57] ABSTRACT

A device for measuring the effective porosity of a sample comprising, a device for defining a cavity defining an opening, a device for sealing the sample around the cavity opening, a device for measuring the internal pressure of the cavity, a device for passing gas into the cavity, a device for measuring the flow rate of the passed gas, and a device for adjusting the flow rate of the passing device until a predetermined value of the internal pressure is obtained in the cavity.

32 Claims, 2 Drawing Sheets

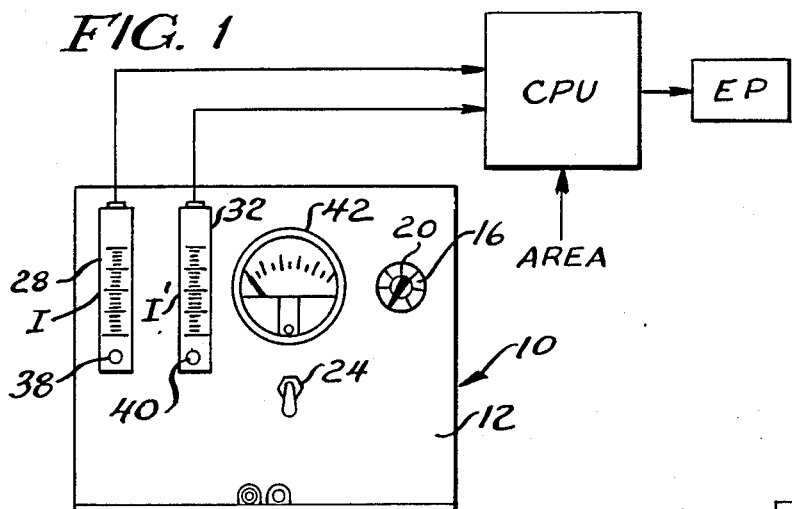
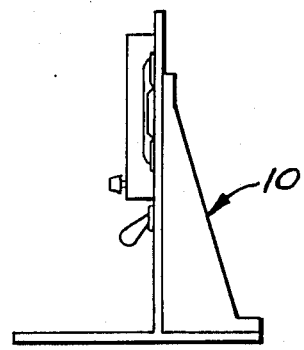
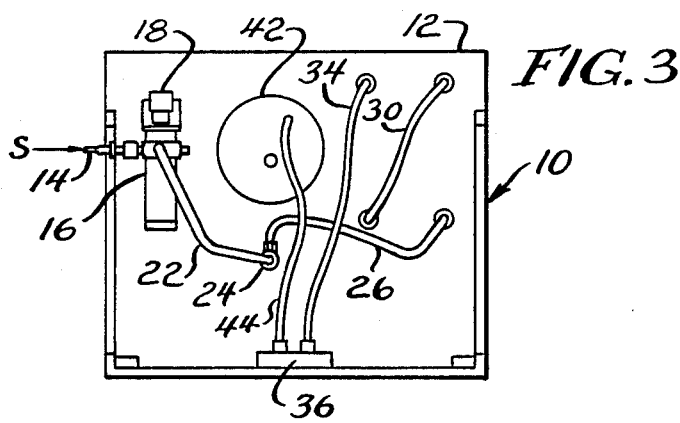
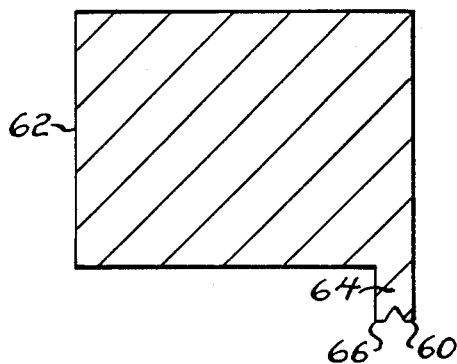
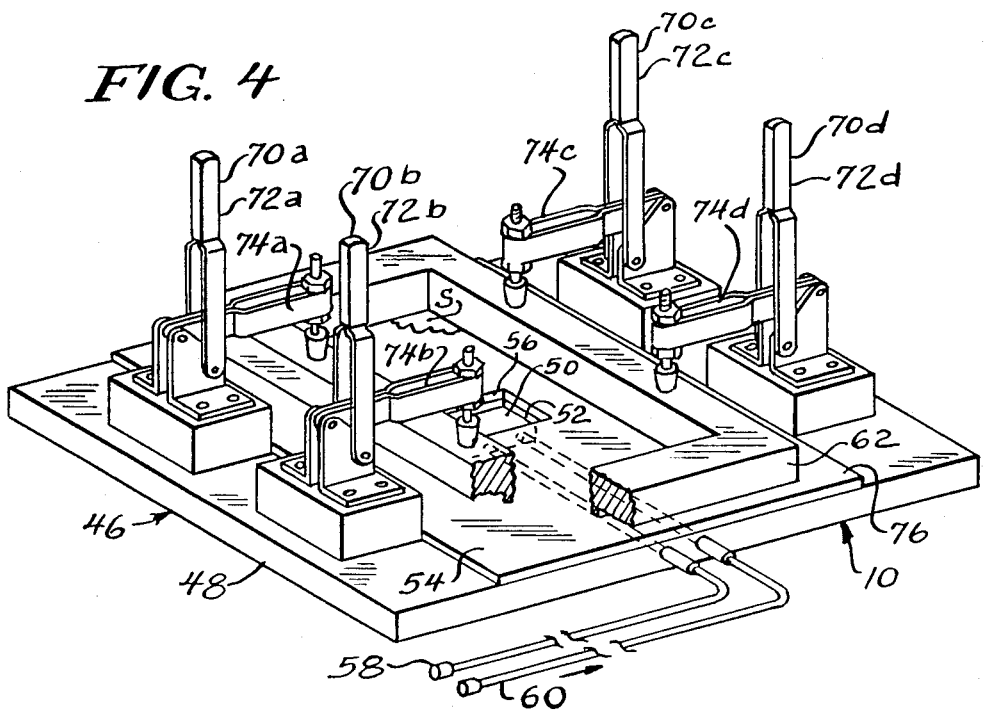

DEVICE FOR MEASURING EFFECTIVE POROSITY

BACKGROUND OF THE INVENTION

The present invention relates to a device for measuring the effective porosity of a sample.

It is frequently desired to measure the porosity of a portion of a package, and particularly sterile packages. The reasons for desiring to determine the porosity of the package include the following: (1) to determine whether the package provides a sterile barrier, (2) to determine whether the package can be sterilized by gas, and (3) to determine the package integrity. Thus, porosity is an important attribute of most medical packages, especially those which contain products which are gas sterilized. In addition to product containment and protection, a package must be able to maintain sterile integrity during normal shipment, storage, and sterilization. Excessively low porosity materials may present good barrier properties, but not be able to withstand normal sterilization pressure changes without package failure. Excessively high porosity materials may withstand pressure changes well, but not be a sterile barrier.

The presently accepted manner of measuring porosity is with a Gurley Densimeter which measures the time necessary for 100 cc of air to pass through one square inch of sample area with a constant pressure of 4.88 inches of water. Results are reported in Gurley Seconds which are the inverse of porosity (i.e. the higher the Gurley Seconds, the lower the porosity). This method is hampered by the small area measured and inherent possibility of contaminating the test sample with oil by the device. A second instrument is the ARO porosity tester which measures porosity in Gurley Seconds using a calibrated pressure of 4.88 inches of water. While this unit does not exhibit the oil contamination potential, it still measures only one square inch of sample (10 square inch attachment is available, but requires multiplication of results to obtain Gurley Seconds), and is prone to mechanical problems which are not always obvious when conducting a test. Problems have been experienced when trying to obtain agreement or correlation between different pieces of test equipment on the same test sample.

SUMMARY OF THE INVENTION

A principal feature of the present invention is the provision of an improved device for measuring effective porosity. In this regard, the device provides an overall porosity of a sample being tested, and is referred to effective porosity to distinguish it from Gurley Seconds.

The device of the present invention comprises, means for defining a cavity defining an opening, means for sealing the sample around the cavity opening, means for measuring the internal pressure of the cavity, means for passing the gas into the cavity, means for measuring the flow rate of the passed gas, and means for adjusting the flow rate of the passing means until a predetermined value of the internal pressure is obtained in the cavity.

Thus, a feature of the present invention is that the effective porosity is determined by measuring flow rate with a fixed internal pressure rather than time to pass a fixed volume of air.

Another feature of the present invention is that the effective porosity measured by the device can be readily correlated to standard Gurley Seconds.

Still another feature of the present invention is that the device may measure a sample of any desired size or shape, rather than being confined to a relatively small area of the sample.

A feature of the present invention is that the device measures the effective porosity in a more accurate manner.

Still another feature of the invention is that the device of the present invention saves substantial time over the standard techniques for measuring effective porosity.

Yet another feature of the invention is that the device may measure the effective porosity in a package, including different orientation of the packages, and may measure the effective porosity during sterilization.

Another feature of the invention is the provision of a method for measuring the effective porosity of a sample.

A further feature of the invention is the provision of a method of checking the accuracy of the flow measurement of the device.

Another feature of the invention is the provision of a method for correlating the flow measurement of the present device to those of standard effective porosity procedures.

Further features will become more fully apparent in the following description of the embodiments of this invention and from the appended claims.

DESCRIPTION OF THE DRAWING

In the drawings:

FIG. 1 is a front elevational view of a control panel of a device for measuring effective porosity of the present invention;

FIG. 2 is a side elevational view of the control panel of FIG. 1;

FIG. 3 is a rear elevational view of the control panel of FIG. 1;

FIG. 4 is a fragmentary perspective view of a device for securing a sample during testing;

FIG. 5 is a sectional view of a sealing member for the device of FIG. 4;

DESCRIPTION OF THE PREFERRED EMBODIMENTS

Figure 6:
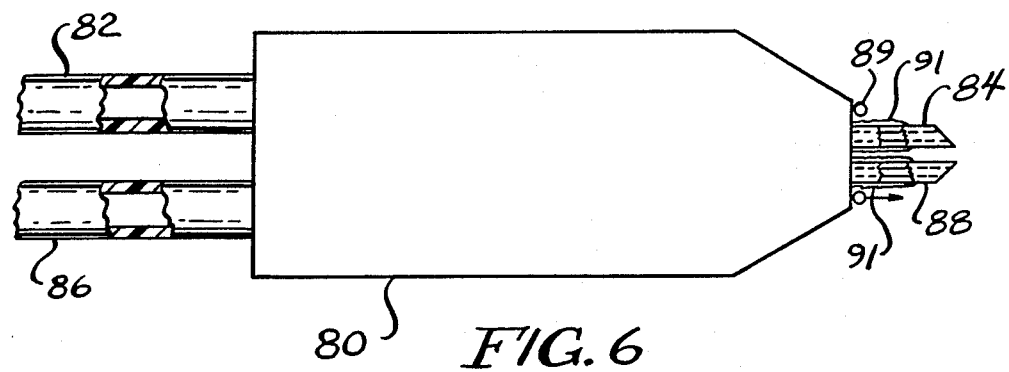
FIG. 6 is a fragmentary plan view, taken partly in section, of a probe for measuring the effective porosity of a package.

Referring now to FIGS. 1-3, there is shown an effective porosity measuring device generally designated 10 having a control panel 12.

The device 10 has an air inlet 14 from a source of pressurized gas or air which passes to a pressure gauge 16 which includes a regulator and filter. The pressure gauge 16 may be adjusted by a knob 18, and the resulting pressure is indicated on a suitable dial 20 which indicates the adjusted pressure.

The pressure gauge 16 is connected by a conduit 22 to an on/off switch 24 which permits or prevents passage of gas depending upon the two positions of the switch 24. The switch 24 is connected by a conduit 26 to the lower end of a first flow meter 28 having indicia I, and the upper end of the first flow meter 28 is connected by a conduit 30 to the lower end of a second flow meter 32 having indicia I', while the upper end of the second flow meter 32 is connected by a conduit 34 to a connector 36. The indicia I and I' on the flow meters 28 and 32 are utilized to indicate the flow rate of the gas.

Although the device is described in connection with two flow meters, it will be understood that only one flow meter is required, or the device may have more than two flow meters connected in series. In the particular form shown, the second flow meter 32 provides a more accurate reading in a wider range on the indicia scale, than the first flow meter 28. The flow meters 28 and 32 have respective knobs 38 and 40 to control the rate of flow of the gas or air through the flow meters 28 and 32. As shown, the flow meters 28 and 32 are electrically connected to a central processing unit (CPU) for a purpose which will be described below.

The control panel 12 has a pressure gauge 42 which is connected by a conduit 44 to the connector 36.

With reference to FIGS. 4 and 5, the measuring device 10 has a sample sealing device generally designated 46. The device 46 has an elongated planar block 48 with a central cavity 50 defining an upwardly facing opening 52. The device 46 has an elastic cover plate of elastomeric gasket material 54, such as silicone or rubber, extending over a substantial upper portion of an upper surface of the block 48, with the cover plate 54 being secured to the block 48, such as by adhesive. As shown, the cover plate 54 has an opening 56 in register with the opening 52 of the block 48.

The device 46 has a first conduit 58 which communicates between the conduit 44 in the connector 36 illustrated in connection with FIGS. 1–3 and the cavity 50, including a bore in the block 48.

The device 46 also has a second conduit 60 which communicates between the conduit 34 in the connector 36 illustrated in connection with FIGS. 1–3 and the cavity 50, including a bore in the block 48.

The device 46 has a sealing member 62 of any desired size extending peripherally around the cavity 50 and opening 56 of the cover plate 54. As shown in FIG. 5, the sealing member 62 has a downwardly extending peripheral flange 64 with a pair of spaced lower sealing lips 66 and 68 for a purpose which will be described below.

The device 46 has a plurality of clamps 70a, 70b, 70c, and 70d of known type with respective handles 72a, 72b, 72c, and 72d which operate respective clamping members 74a, 74b, 74c, and 74d in order to engage against an upper surface of the sealing member 62 and urge the sealing member 62 into sealing engagement against an upper surface 76 of the cover plate 54. Of course, the handles 72a, b, c, and d may be moved to release the associated clamping member 74a, b, c, and d from the sealing member 62 in order to remove the sealing member 62 from the device.

In use, a porous sample S to be tested having a width and length at least as large as the flange or rim 64 is placed on the upper surface 76 of the cover plate 54, and the sealing member 62 is placed over the sample S. Next, the clamps 70a, b, c, and d are operated in order to clamp the sealing member 62 in sealing engagement by the lips 66 and 68 against the sample S on the upper surface 76 of the cover plate 54. Of course, during this time, the elasticity of the cover plate 54 enhances the sealing between the sealing member 62 against the cover plate 54. It will be apparent that the sealing member 62 may be made of any suitable size as small as the opening 56 of the cover plate 54, and sufficiently large to accomodate any desired sample S to be tested, with the size of the sample S being determined by the rim or flange 64. Also, the cavity 50 may be made of any desired size in order to test the sample S. During this time, the lips 66 and 68 of the sealing member 62 provide a maximum seal against the sample S along with minimal pressure in the cavity 50.

When it is desired to test the sample S, the switch 24 is turned to the on position, in order to permit passage of gas through the conduit 22 from the adjusted pressure gauge 16, and through the conduit 26 to the first flow meter 28, and through the conduit 30 to the second flow meter 32. In turn, the gas passes through conduit 34 and conduit 60 into the cavity 50 where the air passes through the openings 50 and 56 beneath the sample S, and through the entire porous sample S inside the sealing flange or rim 64. At the same time, the pressure gauge 42 measures the internal pressure of the cavity 50 through the conduits 44 and 58. The flow meters 28 and 32 are adjusted to produce a rate of flow of gas into the cavity 50 until the sample S reaches equilibrium at a desired internal pressure as determined by the pressure gauge 42, such as an air or gas pressure of 4.88 inches of water, which is preferred since it is a standard for Gurley Seconds. When the desired internal pressure in the cavity is obtained, the rate of flow of gas to the cavity 50 may be determined by the flow meters 28 and 32, and the effective porosity is obtained by the flow meters 28 and 32 which indicate the rate of flow of gas into the cavity 50 when the desired internal pressure is determined by the pressure gauge 42.

In the preferred form, in which the predetermined gas pressure obtained in the cavity 50 is 4.88 inches of water, the effective porosity EP may be calculated in Gurley Seconds by the following formula:

$$EP = (6 \times \text{Area})/\text{Flow Rate},$$

where
- EP is the effective porosity in Gurley seconds,
- Area is the total area of the porous sample in square inches within the flange or rim 64,
- Flow rate is in liters of air per minute as determined by the flow meters 28 and 32, and
- 6 is a constant to convert the results into Gurley Seconds.

In this manner, the effective porosity EP may be readily determined, and may be calculated in the standard Gurley Seconds. With reference to FIG. 1, as previously indicated, the flow meters 28 and 32 are electrically connected to the central processing unit CPU to provide the CPU with the measured flow rate, the area of the sample inside the sealing rim or flange 64 may be input to the central processing unit CPU by the operator, and the central processing unit CPU calculates the effective porosity EP from the above formula which may be automatically indicated on a suitable display EP.

In an alternative form, with reference to FIG. 6, a probe 80 may be utilized for measuring the effective porosity inside a suitable package. In this form, the conduit 44 is connected to a conduit 82 of the probe 80, and the conduit 82 in turn is connected in fluid communication to a sharpened hollow tubular section 84. Also, the conduit 34 is connected to a conduit 86 of the probe, and the conduit 86 in turn is connected in fluid communication to a second sharpened tubular section. As shown, the probe 80 has a sealing ring 89 extending around a proximal end of the tubular sections 84 and 88 in order to seal the probe against the package. Alternatively, the tubular sections 84 and 88 have a sealing substance 91, such as karaya gum or elastic material, extending around the tubular sections in order to seal against the package.

In use of the probe 80, the sharpened tubular sections 84 and 88 are passed through a wall of the package which has a porous lid or section, and the tubular sections 84 and 88 seal against the punctured wall. The gas from the flow meters 28 and 32 pass through the conduit 86 and tubular section 88 into the inside of the package, and through the porous portion of the package, while the internal pressure of the package is determined through tubular section 84, conduit 82, and conduit 44 by the pressure gauge 42. As previously discussed, the flow meters 28 and 32 are adjusted in order to obtain the desired internal pressure in the package as indicated by the pressure gauge 42, after which the effective porosity may be calculated in the package in a manner as previously described.

Figure 7:
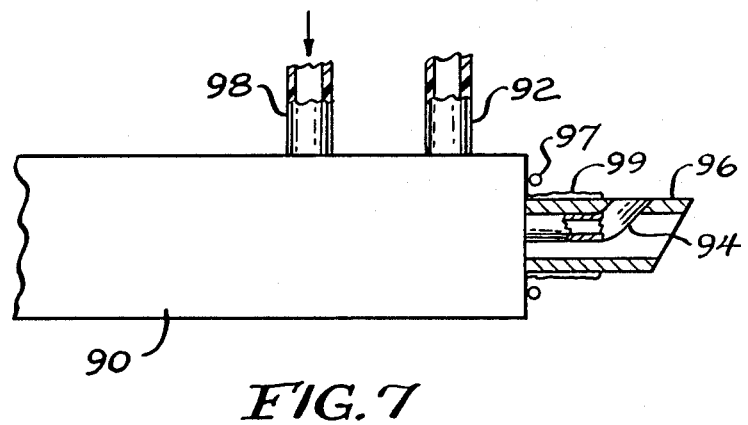
FIG. 7 is a fragmentary plan view taken partly in section, of another embodiment of a probe for measuring the effective porosity of a package.

Another probe 90 for determining the effective porosity in a package is illustrated in FIG. 7. The probe 90 has a conduit 92 which is connected to the conduit 44 associated with the pressure gauge 42, and the conduit 92 is connected in fluid communication with an internal tubular section 94 which passes through a wall of an outer sharpened tubular section 96. The conduit 34 is connected to a conduit 98 of the probe 90, which is connected in fluid communication with the outer hollow tubular section 96. In use, the outer tubular section 96 is passed through a wall of the package until ends of both tubular sections 94 and 96 are located inside the package. As shown, the probe 90 has a sealing ring 97 extending around a proximal end of the tubular section 96 in order to seal the probe against the package. Alternatively, the tubular section 96 may have a sealing substance 99, such as karaya gum or elastic material, extending around the tubular section order to seal against the package. In use, the air or gas passing from the flow meters 28 and 32 pass through the conduit 98 and outer tubular section 96 into the package, and the internal pressure in the package is measured through the tubular section 94, conduit 92, and conduit 44 by the pressure gauge 42, and the effective porosity of the package is determined as previously discussed.

In accordance with the present invention, the accuracy of the flow meters 28 and 32 may be verified in the following manner. First, a nonbreathable sheet is used as the sample in FIG. 4, and is clamped in place. Next, the pressure is increased to 5 inches of water, and the amount of pressure drop is measured in one minute to test for leakage in the total system. If the pressure drops less than one inch in one minute then the leakage is less than 0.01 liter per minute which is finer than the accuracy of reading of normal flow meters 28 and 32 indicating that the device is appropriate for use in testing.

Also, the device may be calibrated and correlated to the Gurley testing device in the following manner. First, a non-porous sheet is constructed with a plurality of small openings which will not change in time. The Gurley device is utilized to measure air flow separately through each of the openings, and the flow rate associated with each of the openings is calculated and added in order to determine the total flow rate through the sheet. Finally, the sheet is mounted as the sample in the device of FIG. 4, and the flow rate of the flow meters 28 and 32 is adjusted to obtain an internal pressure of 4.88 inches of water as determined by the pressure gauge 42, and the flow rate is determined by the flow meter 28 and 32 which should correlate with the calculated flow rate values determined by the Gurley testing device. In this manner, the device of the present invention may be correlated to the Gurley testing device.

The foregoing detailed description is given for clearness of understanding only, and no unnecessary limitations should be understood therefrom, as modifications will be obvious to those skilled in the art.

What is claimed is:

1. A device for measuring the effective porosity of a sample, comprising:
   means for sealing a predetermined surface area on one side of the sample;
   means for measuring the internal pressure on the sealed one side of the sample;
   means for passing a gas to the sealed one side of the sample;
   means for adjusting the flow rate of the passing means until a predetermined value of the internal pressure is obtained in the one side of the sample; and
   means for calculating the effective porosity in Gurley Seconds.

2. The device of claim 1 including means for measuring the flow rate of the passed gas.

3. The device of claim 1 including means for indicating the flow rate of the passed gas.

4. The device of claim 1, wherein the predetermined internal pressure is 4.88 inches of water, and wherein the effective porosity is calculated in Gurley Seconds according to the following formula:

$$EP = (6 \times Area)/\text{Flow Rate},$$

where,
   EP is the effective porosity in Gurley Seconds,
   Area is the area of the sample in square inches within the inside of the sealing means,
   Flow Rate is in liters of gas per minute passed by the passing means, and
   6 is a constant to convert the results into Gurley Seconds.

5. A device for measuring the effective porosity of a package, comprising:
   means for sealing the package;
   means for measuring the internal pressure of the package;
   means for passing a gas into the package;
   means for measuring the flow rate of the passed gas;
   means for adjusting the flow rate of the passing means until a predetermined value of the internal pressure is obtained in the cavity; and
   means for calculating the effective porosity in Gurley Seconds.

6. The device of claim 5 including means for indicating the flow rate of the passed gas.

7. The device of claim 5, wherein the predetermined value of internal pressure is 4.88 inches of water, and wherein the effective porosity is calculated in Gurley Seconds according to the following formula:

$$EP = (6 \times Area)/\text{Flow Rate},$$

where,
   EP is the effective porosity in Gurley Seconds,

Area is the area of a porous portion of the package in square inches,

Flow Rate is in liters of gas per minute passed by the passing means, and 6 is a constant to convert the results into Gurley Seconds.

8. A device for measuring the effective porosity of a sample, comprising:
a block having a cavity defining an opening facing toward an outer surface of the block;
a sealing member for sealing the sample against said outer surface peripherally around the opening;
pressure measuring means;
means for connecting the pressure measuring means in fluid communication with the cavity;
a source of gas;
means for connecting the gas source to the cavity to permit passage of gas from the source into the cavity;
means for measuring the flow rate of the passed gas;
means for adjusting the flow rate of the passed gas until a predetermined value of pressure is determined by the pressure measuring means; and
means for calculating the effective porosity in Gurley Seconds.

9. The device of claim 8 including means for indicating the flow rate of the passed gas.

10. The device of claim 7 wherein the block includes an outer elastic sealing member defining the outer surface of the block.

11. The device of claim 10 wherein the sealing member has an opening in register with the cavity opening.

12. The device of claim 8 wherein the sealing member has a pair of spaced sealing lips extending peripherally around the opening.

13. The device of claim 8 wherein the sealing member seals the sample against the outer surface at a substantial distance from said opening.

14. The device of claim 8 including means for clamping the sealing member against the block.

15. The device of claim 8 wherein the pressure measuring means comprises a pressure gauge.

16. The device of claim 8 wherein the flow rate measuring means comprises at least one flow meter.

17. The device of claim 16 wherein the flow rate measuring means comprises a plurality of flow meters connected in series.

18. A device for measuring the effective porosity of a package, comprising:
a probe having a pair of tubular sections for placement through a wall of the package;
means for sealing said probe to the wall of the package;
pressure measure means;
means for connecting the pressure measuring means in fluid communication with one of the tubular sections;
a source of gas;
means for connecting the gas source to the other tubular section to permit passage of gas from the source to the package;
means for measuring the flow rate of the passed gas;
means for adjusting the flow rate of the passed gas until a predetermined value of pressure is determined by the pressure measuring means; and
means for calculating the effective porosity in Gurley Seconds.

19. The device of claim 18 including means for indicating the flow rate of the passed gas.

20. The device of claim 18 wherein the pressure measuring means comprises a pressure gauge.

21. The device of claim 18 wherein the flow rate measuring means comprises at least one flow meter.

22. The device of claim 21 wherein the flow rate measuring means comprises a plurality of flow meters connected in series.

23. The device of claim 18 wherein the tubular sections are generally aligned and spaced from each other in the probe.

24. The device of claim 18 wherein one of the tubular sections extends through a wall of the other tubular section.

25. A method for measuring the effective porosity of a sample, comprising the steps of:
measuring the internal pressure of a cavity having an opening;
sealing the sample around the opening;
passing a gas into the cavity;
measuring the flow rate of the passed gas;
adjusting the flow rate of the passed gas until a predetermined value of the internal pressure is obtained in the cavity; and
calculating the effective porosity in Gurley Seconds.

26. The method of claim 25 including the step of checking the accuracy of the flow measurement step by using an nonbreathable sample, passing gas at a relatively large pressure into the cavity, and measuring the pressure decrease for a period of time to determine leakage in the system relative to accuracy of the flow measurement step.

27. The method of claim 25 including the step of correlating the flow measurement to a standard effective porosity procedure by using a nonbreathable sample with a plurality of small openings, separately determing the flow rate by the standard procedure for each of the openings, calculating the total flow rate by the standard procedure through all of the openings, and using the nonbreathable sample as said sample to determine the flow rate at a predetermined pressure used by the standard procedure.

28. The device of claim 23 wherein the probe includes a sealing ring extending around a proximal end of the tubular sections.

29. the device of claim 23 wherein the tubular sections include a sealing substance extending around the tubular section.

30. The device of claim 24 wherein the probe includes a sealing ring extending around a proximal end of the other tubular section.

31. The device of claim 24 wherein the other tubular section includes a sealing substance extending around the other tubular section.

32. The device of claim 8, wherein the predetermined value of pressure is 4.88 inches of water, and wherein the effective porosity is calculated in Gurley Seconds accordingly to the following formula:

$$EP = (6 \times Area)/\text{Flow Rate},$$

where,
EP is the effective porosity in Gurley Seconds,
Area is the area of the sample in square inches within the inside of said sealing member,
Flow Rate is in liters of gas per minute passed by the passing means, and
6 is a constant to convert the results into Gurley Seconds.

* * * * *